(12) United States Patent
Seen (10) Patent No.: US 9,000,383 B2
(45) Date of Patent: Apr. 7, 2015

(54) DIGITAL IMAGE DETECTOR AND DIGITAL IMAGE DETECTING METHOD USING GRATINGS

(76) Inventor: Dong June Seen, Seoul (KR)

(*) Notice: Subject to any disclaimer, the term of this patent is extended or adjusted under 35 U.S.C. 154(b) by 0 days.

(21) Appl. No.: 14/122,142

(22) PCT Filed: May 27, 2011

(86) PCT No.: PCT/KR2011/003914
§ 371 (c)(1),
(2), (4) Date: Jan. 27, 2014

(87) PCT Pub. No.: WO2012/161365
PCT Pub. Date: Nov. 29, 2012

(65) Prior Publication Data
US 2014/0151568 A1 Jun. 5, 2014

(30) Foreign Application Priority Data
May 26, 2011 (KR) .................. 10-2011-0050267

(51) Int. Cl.
*G01T 1/20* (2006.01)
*A61B 6/00* (2006.01)

(52) U.S. Cl.
CPC ............. *G01T 1/2002* (2013.01); *A61B 6/4291* (2013.01); *A61B 6/484* (2013.01); *A61B 6/4233* (2013.01)

(58) Field of Classification Search
CPC .................................................... G01N 23/04
USPC ........................................................... 250/368
See application file for complete search history.

(56) References Cited

U.S. PATENT DOCUMENTS

| 4,413,353 A * | 11/1983 | Macovski et al. ................ 378/62 |
| 5,289,012 A * | 2/1994 | Alvarez ......................... 250/588 |
| 2005/0031081 A1 * | 2/2005 | Winsor ......................... 378/98.12 |
| 2009/0101844 A1 * | 4/2009 | Ohbayashi .................. 250/488.1 |
| 2010/0140464 A1 * | 6/2010 | Balistreri et al. ......... 250/237 G |
| 2012/0062901 A1 | 3/2012 | Yoshida et al. |

FOREIGN PATENT DOCUMENTS

| JP | 7-027722 A | 1/1995 |
| JP | 2007-125102 A | 5/2007 |
| JP | 2008-224661 A | 9/2008 |
| JP | 2011/007775 A | 1/2011 |

\* cited by examiner

*Primary Examiner* — Kiho Kim
(74) *Attorney, Agent, or Firm* — Birch, Stewart, Kolasch & Birch, LLP (57) ABSTRACT

A digital image detector and a digital image detecting method using gratings are provided. The digital image detector includes a fluorescent screen that receives X-rays passing through an object, converts the received X-rays into rays and outputs the converted rays, a first reflecting plane that reduces an image based on the rays output from the fluorescent screen in a first axis direction using a grating, a second reflecting plane that reduces the image reduced by the first reflecting plane in a second axis direction using a grating, and an imaging device that receives the image reflected and output from the second reflecting plane, focuses the received image, and converts the focused image into an electrical signal.

10 Claims, 5 Drawing Sheets

DIGITAL IMAGE DETECTOR AND DIGITAL IMAGE DETECTING METHOD USING GRATINGS

TECHNICAL FIELD

The present invention relates to a digital image detector and a digital image detecting method, and more particularly, to a digital image detector and a digital image detecting method using gratings.

BACKGROUND ART

Conventional X-ray imaging devices used to understand states of patients in hospitals have various problems in development and storage of X-ray films on which the states of patients are recorded. In order to solve these problems, digital X-ray imaging devices having a digital image detector mounted thereon have been used more and more.

In general, in a digital image detector, X-rays emitted from an X-ray source pass through an object and is then input to a fluorescent screen. The X-rays input to the fluorescent screen are converted into visible rays and are output from the fluorescent screen.

The output visible rays are reflected by a reflector and are input to a CCD camera. The CCD camera has a CCD (Charge-Coupled Device) which is an imaging device that receives visible rays and converts an image of the visible rays into electrical signals. Therefore, the visible rays input to the CCD camera are focused and are converted into electrical signals.

In such a digital image detector, since sufficient visible rays are not output from the fluorescent screen to which the X-rays are input, the distance from the fluorescent screen to the CCD camera should be minimized. However, the smaller the distance between the fluorescent screen and the CCD camera becomes, the shorter an optical path becomes and the larger an angle at which the fluorescent screen is viewed from the CCD camera, that is, a viewing angle, becomes. When the viewing angle increases, aberrations of an optical system increases in proportion to the viewing angle and it is thus not possible to obtain an excellent image.

SUMMARY OF THE INVENTION

Technical Problem

The present invention is made to solve the above-mentioned problems and an object thereof is to provide a digital image detector which can be formed in a flat shape by solving the above-mentioned problem that the optical path should be kept long in the digital image detector and a digital image detecting method thereof.

Other objects of the present invention will become more apparent in conjunction with embodiments to be described below.

Solution to Problem

According to the solution to the problem, the problem that the optical path should be kept long in a digital image detector can be solved by forming an image which are sufficiently reduced in a vertical direction and a horizontal direction through the use of reflecting planes with gratings to minimize a viewing angle or directly transmitting an image which are sufficiently reduced in a vertical direction and a horizontal direction through the use of reflecting planes with gratings to an imaging device in a one-to-one manner.

According to an aspect of the present invention, there is provided a digital image detector with gratings, including: a fluorescent screen that receives X-rays passing through an object, converts the received X-rays into rays and outputs the converted rays; a first reflecting plane that reduces an image based on the rays output from the fluorescent screen in a first axis direction using a grating; a second reflecting plane that reduces the image reduced by the first reflecting plane in a second axis direction using a grating; and an imaging device that receives the image reflected and output from the second reflecting plane, focuses the received image, and converts the focused image into an electrical signal.

The digital image detector according to the aspect of the present invention may include one or more of the following features. For example, the first reflecting plane may reduce the image output from the fluorescent screen in a vertical direction and the second reflecting plane may reduce the image output from the first reflecting plane in a horizontal direction. The first reflecting plane may reduce the image output from the fluorescent screen in a horizontal direction and the second reflecting plane may reduce the image output from the first reflecting plane in a vertical direction.

A reflecting portion having a constant brazed angle may be formed on the front surfaces of the gratings. Slits having a constant brazed angle may be formed in the gratings.

The image reflected and output from the second reflecting plane may be input to the imaging device after passing through a total reflection prism.

According to another aspect of the present invention, there is provided a digital image detecting method with gratings, including the steps of: receiving X-rays passing through an object and converting the received X-rays into a light beam; reducing an image based on the converted light beam in a first axis direction using a grating; reducing the image reduced by the first reflecting plane in a second axis direction using a grating; and converting the image reduced in the second axis direction into an electrical signal.

The digital image detecting method according to the aspect of the present invention may include one or more of the following features. For example, the step of reducing the image in the first axis direction may include reducing the image in a horizontal direction, and the step of reducing the image in the second axis direction may include reducing the image in a vertical direction. The step of reducing the image in the first axis direction may include reducing the image in a vertical direction, and the step of reducing the image in the second axis direction may include reducing the image in a horizontal direction.

The X-rays passing through the object may be converted into any of visible rays, infrared rays, and ultraviolet rays.

Advantageous Effects of the Invention

By employing the digital image detector and the digital image detecting method according to the present invention, a light beam output from the fluorescent screen is reduced in the first axis direction through the use of the first reflecting plane with the grating and is reduced in the second axis direction through the use of the second reflecting plane with the grating, whereby it is possible to reduce aberrations of an optical system by minimizing the viewing angle regardless of the distance from the fluorescent screen to the imaging device.

The conventional digital image detector has required a considerable internal space for securing an optical path. However, in the digital image detector or the digital image detecting method according to the present invention, since it is not necessary to secure such an optical path by employing the

BRIEF DESCRIPTION OF THE DRAWINGS

FIG. 8 is a side view of a first reflecting plane illustrated in FIG. 7.

FIG. 9 is a flowchart illustrating a digital image detecting method according to still another embodiment of the present invention.

DESCRIPTION OF EMBODIMENTS

The invention can be modified in various forms and can have various embodiments. Specific embodiments will be illustrated in the drawings and described in detail. However, the embodiments are not intended to limit the invention, but it should be understood that the invention includes all modifications, equivalents, and replacements belonging to the concept and the technical scope of the invention. When it is determined that detailed description of known techniques involved in the invention makes the gist of the invention obscure, the detailed description thereof will not be made.

The terms used in the following description are intended to merely describe specific embodiments, but not intended to limit the invention. An expression of the singular number includes an expression of the plural number, so long as it is clearly read differently. The terms such as "include" and "have" are intended to indicate that features, numbers, steps, operations, elements, components, or combinations thereof used in the following description exist and it should thus be understood that the possibility of existence or addition of one or more other different features, numbers, steps, operations, elements, components, or combinations thereof is not excluded.

Terms such as "first" and "second" can be used to describe various elements, but the elements are not limited to the terms. These terms are used only for distinguishing one element from another element.

Hereinafter, embodiments of the invention will be described in detail with reference to the accompanying drawings. In describing the invention with reference to the accompanying drawings, like elements are referenced by like reference numerals or signs regardless of the drawing numbers and description thereof is not repeated.

Figure 1:
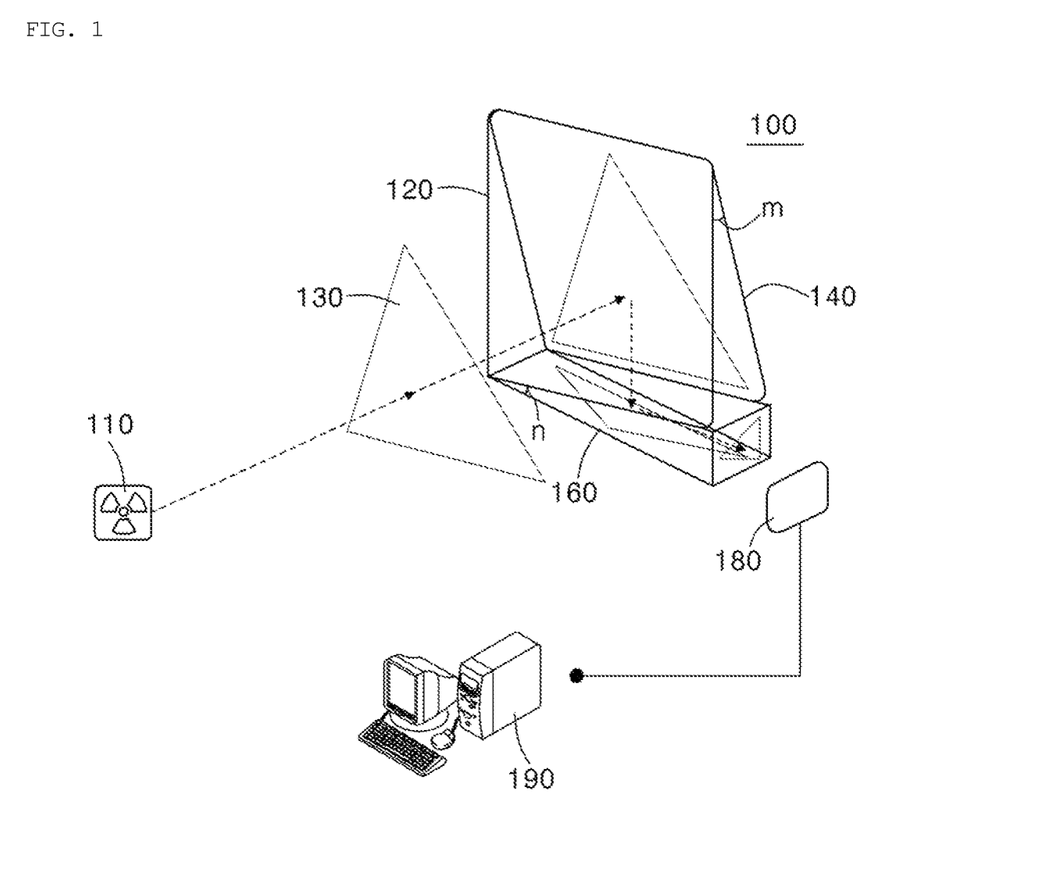
FIG. 1 is a perspective view illustrating a digital image detector according to an embodiment of the present invention.
Figure 2:
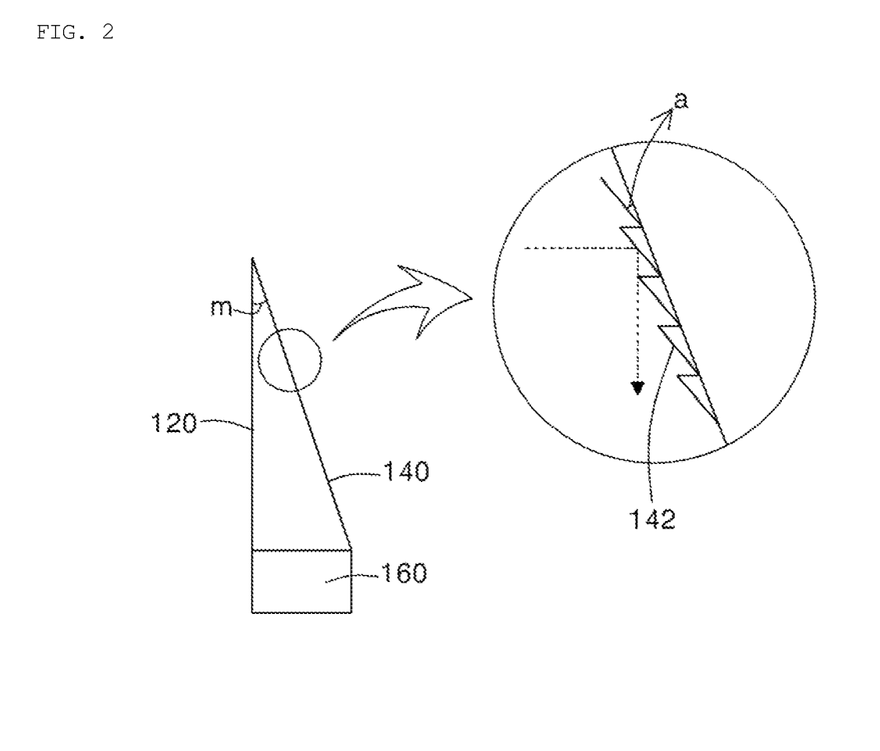
FIG. 2 is a side view of a first reflecting plane illustrated in FIG. 1.
Figure 3:
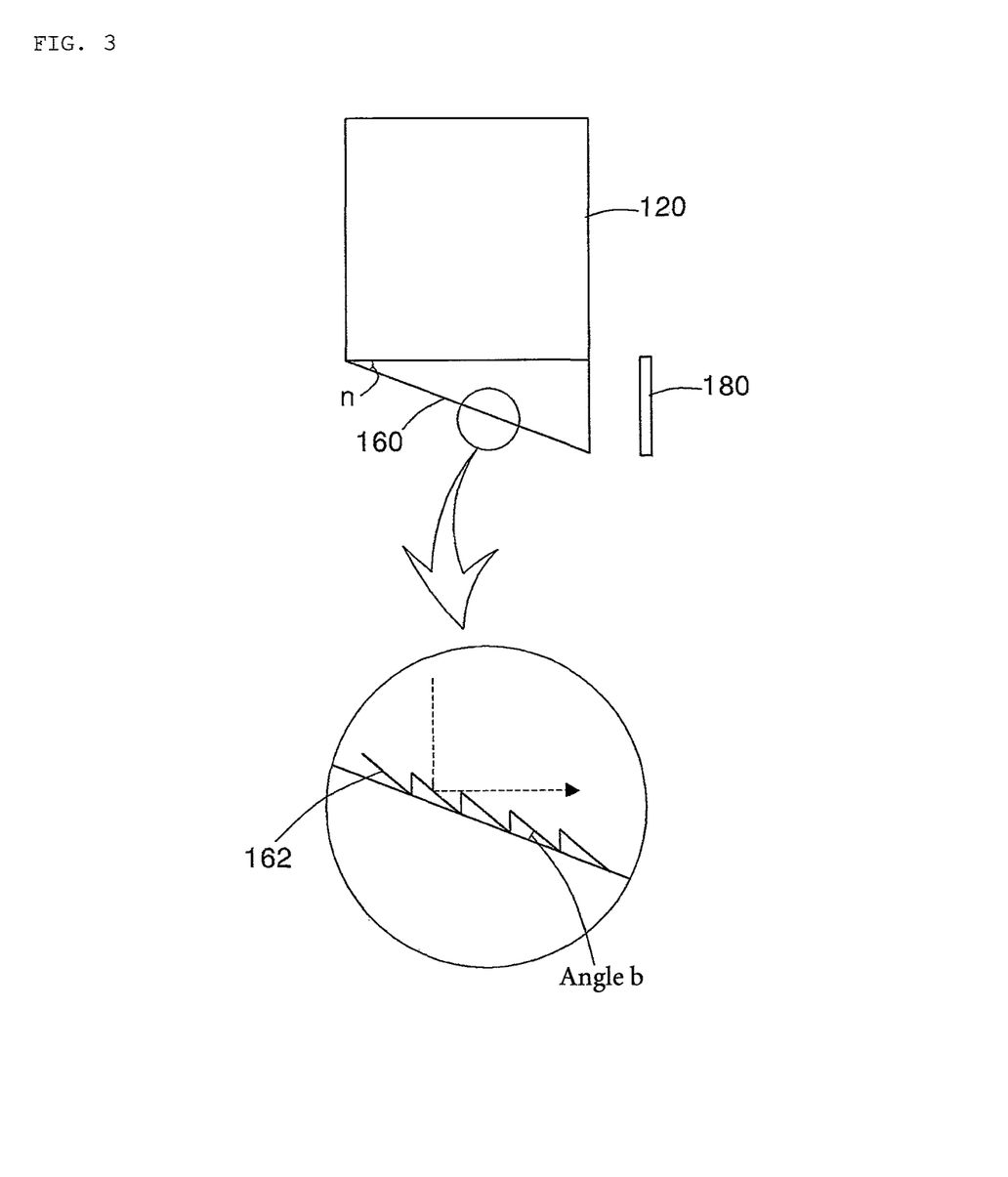
FIG. 3 is a side view of a second reflecting plane illustrated in FIG. 1.
Figure 4:
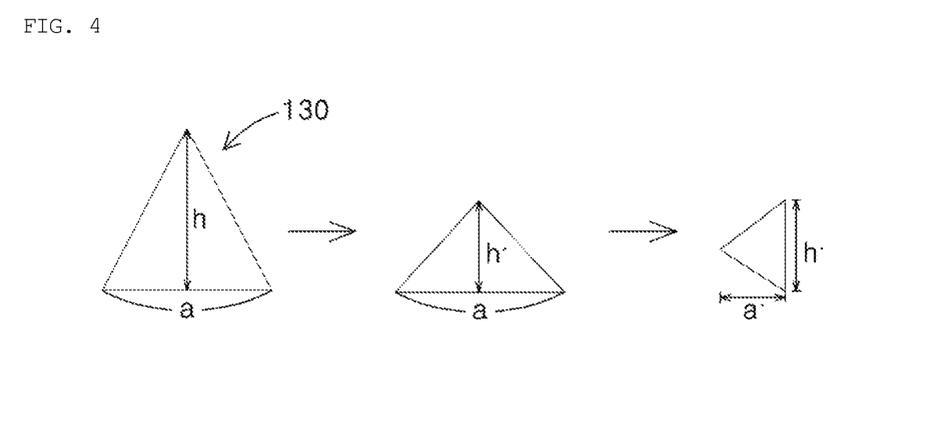
FIG. 4 is a diagram illustrating processes of reducing an image emitted from a fluorescent screen in a first axis direction and a second axis direction in the digital image detector illustrated in FIG. 1.

FIG. 1 is a perspective view illustrating a digital image detector 100 according to an embodiment of the present invention. FIG. 2 is a side view of a first reflecting plane 140 illustrated in FIG. 1. FIG. 3 is a side view of a second reflecting plane 160 illustrated in FIG. 1. A grating is enlarged in circles of FIGS. 1 to 3. FIG. 4 is a diagram illustrating processes of reducing an image emitted from a fluorescent screen 120 in a first axis direction (vertical direction) and a second axis direction (horizontal direction), which are perpendicular to each other, in the digital image detector 100 illustrated in FIG. 1.

Referring to FIGS. 1 to 4, the digital image detector 100 according to this embodiment includes a fluorescent screen 120 that receives an image 130 based on X-rays passing through an object (not illustrated) out of X-rays emitted from an X-ray source 110, converts the image into a light beam, and outputs the light beam, a first reflecting plane 140 that reduces the image based on the light beam output from the fluorescent screen 120 in a vertical axis direction using a grating, a second reflecting plane 160 that reduces the image reduced by the first reflecting plane 140 in a horizontal axis direction again, and an imaging device 180 that receives the image reflected and output from the second reflecting plane 160, focuses the received image, and converts the focused image into an electrical signal.

In the digital image detector 100 according to this embodiment, the image 130 of the object output from the fluorescent screen 120 is reduced in the vertical axis direction corresponding to the first axis direction through the reflecting plane 140 using a grating. The image reduced in the vertical axis direction is reduced in the horizontal axis direction corresponding to the second axis direction through the second reflecting plane 160 using a grating. Therefore, the digital image detector 100 according to this embodiment can reduce aberrations of an optical system by minimizing a viewing angle regardless of the distance from the fluorescent screen 120 to the imaging device 180 and can minimize an internal space for securing an optical path by the use of the reflecting planes using the gratings to construct the detector in a flat pane shape.

The fluorescent screen 120 receives the image 130 of the X-rays passing through an object (not illustrated) and outputs visible rays corresponding thereto. Fluorescent particles (not illustrated) are finely dispersed in the fluorescent screen 120. The fluorescent particles are excited by the X-rays to generate visible rays. The fluorescent screen 120 may output ultraviolet rays or infrared rays in addition to the visible rays. In this case, the imaging device 180 may be constructed as a device that can convert the ultraviolet rays or the infrared rays into an electrical signal.

The first reflecting plane 140 is disposed with a constant inclination angle m with respect to the fluorescent screen 120 located vertically. The first reflecting plane 140 and the fluorescent screen 120 both have a rectangular shape. The upper side of the first reflecting plane 140 comes in contact with the upper side of the fluorescent screen 120. The image 130 passing through the object is incident on the first reflecting plane 140.

The first reflecting plane 140 is formed of a grating. In general, a grating is an optical element in which several tens to several hundreds of grooves per 1 mm are formed on a glass or plastic plate with a diamond bit. Such a grating is used to select a wavelength of light mainly using diffraction and interference of light. An Echelette grating out of such gratings is a grating in which plural reflecting portions 142 having a sawtooth shape are formed with a constant gap as illustrated in FIG. 2 and can adjust incident light and diffracted light using a brazed angle a. Referring to FIGS. 2 and 3, the brazed angle a of the first reflecting plane 140 is set to cause the incident light and the diffracted light to form 90 degrees.

In the digital image detector 100, X-rays emitted from the X-ray source 110 passes through an object and then are input to the fluorescent screen 120. The X-rays input to the fluorescent screen 120 are converted into visible rays and then are output from the fluorescent screen 120.

The visible rays output from the fluorescent screen 120 are mainly of a monochromatic type. Therefore, the use of the grating causes an effect of reflecting the brazed angle a instead of the effect of dispersing a spectrum of light. An effect of reducing an image with respect to one axis such as the vertical axis or the horizontal axis depending on the magnitude of the brazed angle a can be achieved.

Referring to FIG. 2, the incident light input to the first reflecting plane 140 is reflected vertically downward (in parallel to the fluorescent screen 120) by the reflecting portions 142 of the grating and is input to the second reflecting plane 160. In this course, the image 130 of the object is not changed in the horizontal direction but the height thereof is reduced from h to h' in the vertical direction.

The second reflecting plane 160 is formed of an Echelette grating. The reflecting portions 162 formed on the second reflecting plane 160 have a constant brazed angle b. Referring to FIGS. 2 and 3, the second reflecting plane 160 is disposed to cross the first reflecting plane 140 at an angle of 90 degrees and has a constant inclination angle n.

The diffracted light output from the first reflecting plane 140 is incident on the second reflecting plane 160, is reflected by the reflecting portions 162, is changed to diffracted light forming 90 degrees about the incident light, and is then incident on the imaging device 180. Light incident on the fluorescent screen 120 and light incident on the imaging device 180 are orthogonal to each other. The horizontal width of the image 130 of the object is reduced from a to a' in a state where the vertical height h' is maintained by the second reflecting plane 160.

Therefore, referring to FIG. 4, the image 130 of the object is reduced in the vertical direction corresponding to the first axis direction (from h to h') through the reflection by the first reflecting plane 140, and is reduced in the horizontal direction corresponding to the second axis direction through the reflection by the second reflecting plane 160.

In this way, by employing the dual configuration of the first reflecting plane 140 and the second reflecting plane 160 using the gratings, it is possible to obtain an image reduced in the vertical axis direction corresponding to the first axis direction and the horizontal axis direction corresponding to the second axis direction. At this time, by adjusting the brazed angles a and b of the first reflecting plane 140 and the second reflecting plane 160 so that the input light of the first reflecting plane 140 and the diffracted light of the first reflecting plane 140 form 90 degrees, the diffracted light of the first reflecting plane 140 becomes the input light of the second reflecting plane 160, the input light of the second reflecting plane 160 and the diffracted light of the second reflecting plane 160 form 90 degrees, and the diffracted of the second reflecting plane 160 becomes the input light of the imaging device 180, light of which interference is suppressed as much as possible is incident on the imaging device 180, thereby obtaining an excellent image.

Figure 5:
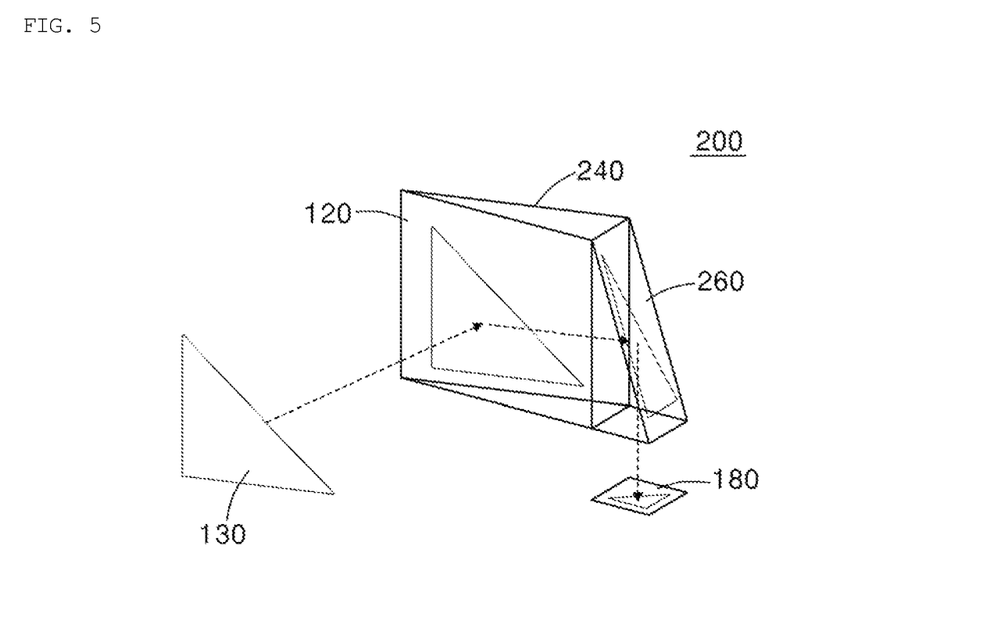
FIG. 5 is a perspective view illustrating a digital image detector according to another embodiment of the present invention.
Figure 6:
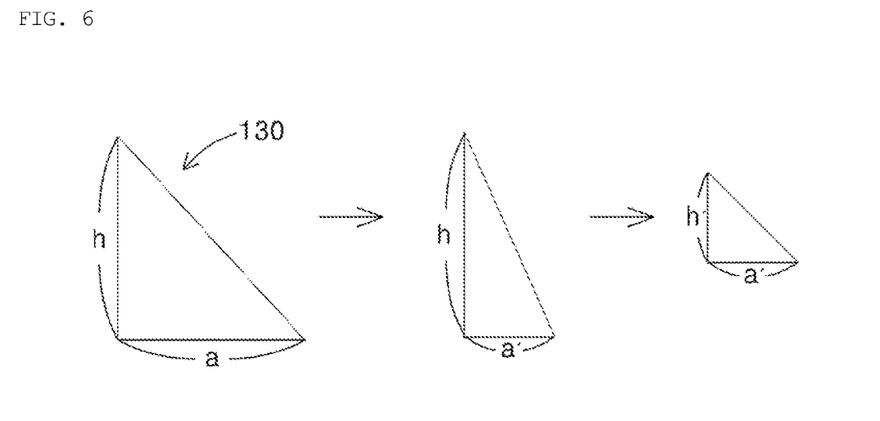
FIG. 6 is a diagram illustrating processes of reducing an image emitted from a fluorescent screen in a first axis direction and a second axis direction in the digital image detector illustrated in FIG. 5.

FIG. 5 is a perspective view illustrating a digital image detector 200 according to another embodiment of the present invention. FIG. 6 is a diagram illustrating a state where an image 130 of an object illustrated in FIG. 5 is reduced by the use of a first reflecting plane 240 and a second reflecting plane 260.

Referring to FIGS. 5 and 6, the digital image detector 200 according to this embodiment includes a fluorescent screen 120 that receives an image 130 based on X-rays passing through an object (not illustrated) out of X-rays emitted from an X-ray source 110, converts the image into a light beam, and outputs the light beam, a first reflecting plane 240 that reduces the image based on the light beam output from the fluorescent screen 120 in the horizontal axis direction using a grating, a second reflecting plane 260 that reduces the image reduced by the first reflecting plane 240 in the vertical axis direction again, and an imaging device 180 that receives the image reflected and output from the second reflecting plane 260, focuses the received image, and converts the focused image into an electrical signal.

In the digital image detector 200 according to this embodiment, the first reflecting plane 240 reduces the image 130 of the object in the horizontal axis direction corresponding to the first axis direction and the second reflecting plane 260 reduces the image of the object reduced in the horizontal axis direction in the vertical axis direction.

The first reflecting plane 240 is disposed with a constant inclination angle one side of the rectangular fluorescent screen 120. The first reflecting plane 240 uses a grating similarly to the first reflecting plane 140 described above and causes the incident light and the diffracted light of the first reflecting plane 240 to form 90 degrees by adjusting the brazed angle of the grating.

The width of the image 130 of the object is reduced from a to a' in the vertical axis direction corresponding to the first axis direction in the course of incidence and reflection on the first reflecting plane 240.

The second reflecting plane 260 is disposed on a plane perpendicular to the fluorescent screen 120 with an inclination angle about one side of the rectangular fluorescent screen 120. The second reflecting plane 260 uses a grating similarly to the first reflecting plane 240 and causes the incident light and the diffracted light of the second reflecting plane 260 to form 90 degrees by adjusting the brazed angle of the grating The height of the image 130 of the object reduced in the horizontal direction by the first reflecting plane 240 is reduced from h to h' in the vertical direction corresponding to the second axis direction in the course of incidence and reflection on the second reflecting plane 260.

Figure 7:
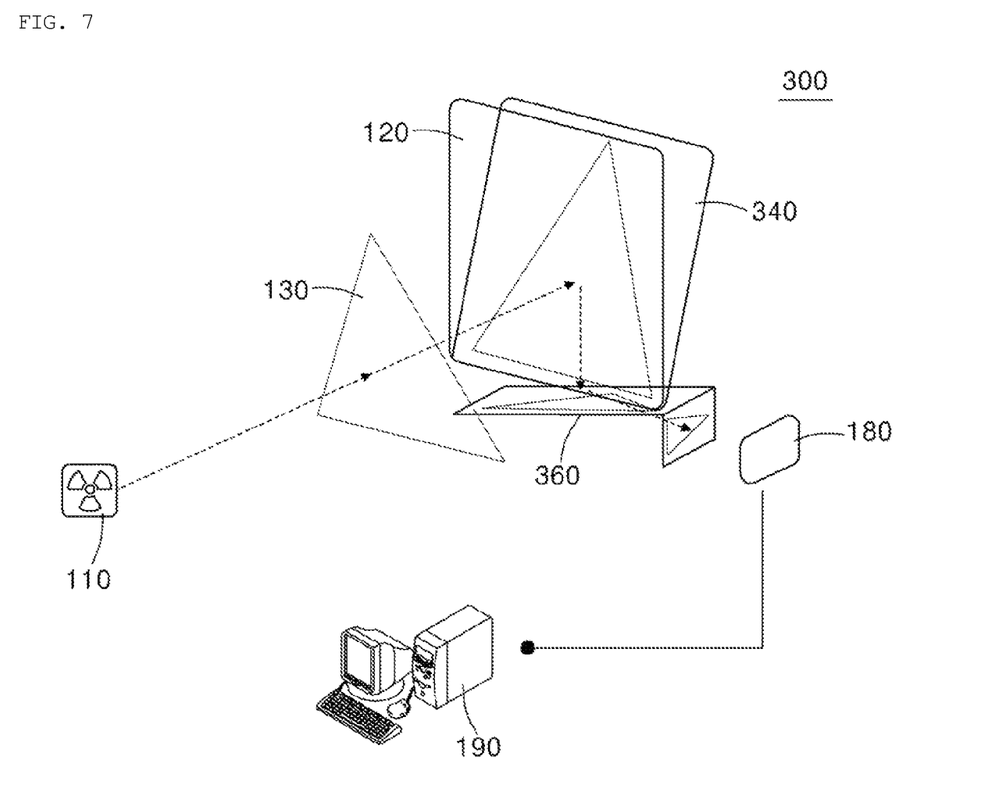
FIG. 7 is a perspective view illustrating a digital image detector according to still another embodiment of the present invention.

FIG. 7 is a perspective view illustrating a digital image detector 300 according to still another embodiment of the present invention. FIG. 8 is a side view of the digital image detector 300 illustrated in FIG. 7.

In the digital image detector 300 illustrated in FIGS. 7 and 8, a first reflecting plane 340 and a second reflecting plane 360 are both formed of a slit grating. The first reflecting planes 140 and 240 and the second reflecting planes 160 and 260 of the digital image detectors 100 and 200 according to the above-mentioned embodiments are formed of an Echelette grating having a sawtooth-like reflecting portions formed thereon and reflection is carried out from the front surface. However, in the first reflecting plane 240 and the second reflecting plane 260 according to this embodiment, reflection is carried out from inner surfaces of the slits 342.

In the digital image detectors 100, 200, and 300 according to the above-mentioned embodiments, the diffracted light of the image of the object reduced in the horizontal and vertical directions is input to the imaging device 180 and the imaging device 180 converts the input light into a digital image and outputs the digital image. The imaging device 180 may be, for example, a CCD (Charge Coupled Device) camera or a CMOS (Complementary Metal-Oxide Semiconductor) camera and is not particularly limited as long as it can convert an image into an electrical signal.

The digital image output from the imaging device 180 is transmitted to a storage device 190 such as a personal computer.

The image of the object reduced in the horizontal and vertical directions by the first reflecting planes 140, 240, and 340 and the second reflecting planes 160, 260, and 360 may be input to the imaging device 180 after passing through a total reflection prism (not illustrated). In the first reflecting planes 140 and 240 and the second reflecting planes 160 and 260 using the Echelette grating, light may be scattered at ends of the sawtooth shapes. Since such scattered light is not reflected perpendicularly to the incidence direction, the scattered light causes degradation of quality of the reduced image. Therefore, such scattered light can be removed using the total reflection prism which reflects only light incident perpendicularly thereon.

FIG. 9 is a flowchart illustrating an image detecting method according to still another embodiment of the present invention.

Referring to FIG. 9, the image detecting method using the grating according to this embodiment includes a step of receiving X-rays passing through an object and converting the X-rays into a light beam, a step of reducing an image based on the converted light beam in the first axis direction using the grating, a step of reducing the image reduced in the first axis direction in the second axis direction using the grating, and a step of converting the image reduced in the second axis direction into an electrical signal.

The step of receiving X-rays passing through an object and converting the received X-rays into a light beam such as visible rays is generally performed by the fluorescent screen 120. The X-rays passing through an object may be converted into infrared rays or ultraviolet rays in addition to the visible rays.

The image based on the converted light beam is reduced in the first axis direction by the first reflecting plane 140, 240, or 340 using a grating, and is reduced in the second axis direction by the second reflecting plane 160, 260, or 360. The first axis direction may be one of the horizontal direction and the vertical direction with respect to the front surface of the fluorescent screen 120, and the second axis direction may be the other of the horizontal direction and the vertical direction with respect to the fluorescent screen 120. As described above, the image 130 of an object may be reduced in the horizontal direction and then may be reduced in the vertical direction or may be reduced in the reverse order depending on the arrangement direction of the first reflecting plane 140, 240, or 340 and the second reflecting plane 160, 260, or 360.

In this way, the image of an object reduced in the first axis direction (horizontal or vertical direction) and the second axis direction (vertical or horizontal direction) perpendicular to each other is captured and converted into an electrical signal by the imaging device 180 embodied by a CCD camera or a CMOS camera.

While the present invention is described above with reference to the embodiments, it will be understood by those skilled in the art that the invention can be modified and changed in various forms without departing from the spirit and scope of the invention described in the appended claims.

REFERENCE SIGNS LIST 100, 200, 300: DIGITAL IMAGE DETECTOR
110: x-RAY SOURCE
120: FLUORESCENT SCREEN
130: OBJECT IMAGE
140, 240, 340: FIRST REFLECTING PLANE
160, 260, 360: SECOND REFLECTING PLANE
180: IMAGING DEVICE
190: STORAGE DEVICE

The invention claimed is:

1. An image detector with gratings, comprising:
a fluorescent screen that receives X-rays passing through an object, converts the received X-rays into a light beam and outputs the converted light beam;
a first reflecting plane that reduces an image based on the light beam output from the fluorescent screen in a first axis direction using a grating;
a second reflecting plane that reduces the image reduced by the first reflecting plane in a second axis direction using a grating; and
an imaging device that receives the image reflected and output from the second reflecting plane, focuses the received image, and converts the focused image into an electrical signal.

2. The image detector with gratings according to claim 1, wherein the first reflecting plane reduces the image output from the fluorescent screen in a vertical direction and the second reflecting plane reduces the image output from the first reflecting plane in a horizontal direction.

3. The image detector with gratings according to claim 1, wherein the first reflecting plane reduces the image output from the fluorescent screen in a horizontal direction and the second reflecting plane reduces the image output from the first reflecting plane in a vertical direction.

4. The image detector with gratings according to claim 1, wherein a reflecting portion having a constant brazed angle is formed on the front surfaces of the gratings.

5. The image detector with gratings according to claim 1, wherein slits having a constant brazed angle are formed in the gratings.

6. The image detector with gratings according to claim 1, wherein the image reflected and output from the second reflecting plane passes through a total reflection prism.

7. An image detecting method with gratings, comprising the steps of:
receiving X-rays passing through an object and converting the received X-rays into a light beam;
reducing an image based on the converted light beam in a first axis direction using a grating;
reducing the image reduced by the first reflecting plane in a second axis direction using a grating; and
converting the image reduced in the second axis direction into an electrical signal.

8. The image detecting method with gratings according to claim 7, wherein the step of reducing the image in the first axis direction includes reducing the image in a horizontal direction, and
wherein the step of reducing the image in the second axis direction includes reducing the image in a vertical direction.

9. The image detecting method with gratings according to claim 7, wherein the step of reducing the image in the first axis direction includes reducing the image in a vertical direction, and
wherein the step of reducing the image in the second axis direction includes reducing the image in a horizontal direction.

10. The image detecting method with gratings according to claim 7, wherein the X-rays passing through the object are converted into any of visible rays, infrared rays, and ultraviolet rays.

* * * * *